United States Patent [19]

Fan

[11] Patent Number: 4,774,183
[45] Date of Patent: Sep. 27, 1988

[54] PROCESS FOR PRODUCING FRUCTOSE

[75] Inventor: Liang-tseng Fan, Manhattan, Kans.

[73] Assignee: Kansas State University Research Foundation, Manhattan, Kans.

[21] Appl. No.: 938,372

[22] Filed: Dec. 8, 1986

Related U.S. Application Data

[63] Continuation of Ser. No. 509,213, Jun. 29, 1983, abandoned.

[51] Int. Cl.[4] ........................ C12P 19/02; C12P 19/24; C12R 1/645
[52] U.S. Cl. ...................................... 435/105; 435/94; 435/803; 435/911; 127/46.1; 127/46.2; 127/58; 127/61
[58] Field of Search .................... 435/94, 98, 102, 105, 435/201, 262, 276, 803, 911; 127/46.1, 58, 61, 46.2

[56] References Cited

U.S. PATENT DOCUMENTS

3,784,409 1/1974 Nelson et al. ...................... 435/94 X
4,276,379 6/1981 Heady .............................. 435/193 X

FOREIGN PATENT DOCUMENTS

160479 12/1975 Japan .................................... 435/105
23193 2/1979 Japan .................................... 435/105

OTHER PUBLICATIONS

*Bergey's Manual of Determinative Bacteriology*, 8th Ed. Buchanan et al. (Eds.), The Williams and Wilkins Co., Baltimore (1974), pp. 512–566.
*The Yeasts*, Lodder (Ed.), North-Holland Publishing Co., London (1970), p. 1309.
Shipman, R. H. and Fan, L. T., "Bio-Plastics and SCP from Starch and Agricultural Wastes, vol. 13, #3, Process Biochemistry 1978, pp. 29–21.
Strandberg, G. W. and Smiley, K. L., "Free and Immobilized Glucose Isomerase from Streptomyecs Phaechromogenes", vol. 21, #4, Applied Microbiology, 1971, pp. 588–593.
Whitesides, G. M. and Wong, C. H., "Enzymes as Catalysts in Organic Synthesis, vol. 16, #2, Aldrichimica Acts 1983, pp. 27–34.

*Primary Examiner*—Esther M. Kepplinger
*Attorney, Agent, or Firm*—Hovey, Williams, Timmons & Collins

[57] ABSTRACT

A low cost process for producing concentrated fructose is described which involves selective, preferential biological utilization of glucose in mixtures of glucose and fructose, in order to thereby yield concentrated fructose. Broadly speaking, the method involves contacting a mixture containing respective amounts of glucose and fructose with a microorganism which preferentially utilizes glucose as compared with fructose, incubating the mixture until the relative concentration of fructose is substantially in excess of that of glucose, and recovering concentrated fructose. In preferred forms, the microorganism is *Pullularia pullulans*, and the starting material may be a mixture of gluctose and fructose, sucrose, a carbohydrate such as inulin or starch; in the latter instances, the *P. pullulans*, by virtue of excretion of invertase, acts to degrade the starting material to give the desired glucose-fructose mixture. Recovery procedures such as ion exchange, evaporation and/or crystallization give highly concentrated or essentially pure fructose. A biopolymer side product resulting from glucose utilization by the preferred microorganism can also be recovered if desired.

15 Claims, 2 Drawing Sheets

PROCESS FOR PRODUCING FRUCTOSE

This application is a continuation, of application Ser. No. 509,213, filed June 29, 1983 now abandoned.

BACKGROUND OF THE INVENTION

1. Field of the Invention

The present invention is concerned with a process for producing concentrated fructose using relatively low cost starting materials and processing steps. More particularly, the method of the present invention is based upon a newly discovered, selective, preferential biological utilization or metabolism of glucose in mixtures of glucose and fructose.

2. Description of the Prior Art

Fructose has always occurred in man's food systems since it is found in the free form in almost all sweet fruits and berries. About fifty percent of the dry matter of honey, the oldest sweetener known to man, is fructose. In recent years however, there has been an increasing interest in the use of fructose, as opposed to sucrose, in various foods. The reasons for this interest are many, including: (1) diabetics must avoid sucrose in their diet, and therefore the use of fructose provides an attractive alternative; (2) sucrose-containing snacks, especially those which remain long in the mouth, have proved harmful to teeth; (3) the safety of using the synthetic sweeteners such as saccharine and cyclamate, has been questioned; and (4) the less pleasant taste of the synthetic sweetners (side- and after-taste) is unpopular with many customers.

Fructose, being a reducing keto-hexose, differs considerably from the non-reducing disaccharide, sucrose, in many of its chemical and physical properties. Fructose is the most water soluble of all of the sugars, but is rather difficult to crystallize, because of the existence of a mixture of tautomers in solution at equilibrium. The sweetness of crystalline fructose is nearly twice that of sucrose, and it is known that mixtures of fructose and saccharine or cyclamate produces a synergistic effect that can be used to advantage, especially in dietetic drinks. Moreover, the use of fructose in special products as an alternative to sucrose is warranted by its partly insulin-independent metabolism, which makes fructose a desirable sweetener in diabetic diets.

While the advantages of fructose use in food systems are many, widespread fructose usage has been thwarted because of the relatively high cost thereof. For example, in 1980 fructose was up to four times more expensive that sucrose. The principal reason for this cost differential stems from the fact that it is very difficult to obtain highly concentrated and/or crystalline fructose. Typical conventional processes, such as fractional crystallization, are very tedious and expensive. Accordingly, while crystalline fructose and solutions containing pure or nearly pure fructose are highly desired by the food industry, and particularly the beverage industry, products are in short supply and relatively expensive.

Accordingly, there is a real and heretofore unsatisfied need in the art for an improved process which will yield concentrated fructose, either in the form of a concentrated solution or as crystalline fructose, at a cost which will make fructose more competitive with traditional sugar.

SUMMARY OF THE INVENTION

The problems outlined above are in large measure solved by the present invention which provides a unique process for producing highly concentrated fructose. Broadly speaking, the method of the invention comprises the steps of contacting the material which includes respective quantities of fructose and glucose with a microorganism characterized by the property of preferentially utilizing glucose as compared with fructose, followed by incubation of the microorganismcontacted material under conditions for causing the microorganism to preferentially utilize the glucose. The incubation of the material is terminated when the concentration of fructose as compared with glucose is at a desired level. The final step of the preferred method involves recovering concentrated fructose.

Advantageously, the microorganism employed in the invention is taken from the class of Fungi Imperfecti, and most preferably is *Pullularia pullulans*. However, other microorganisms having the necessary property of preferential utilization of glucose as compared with fructose may be useful in the context of the invention.

The starting material for the process containing respective quantities of fructose and glucose can be obtained simply by admixing the materials, typically in aqueous solution. However, in other forms of the invention the fructose-glucose mixture can be obtained by degradation of a precursor material. For example, a starting solution of sucrose can be utilized in accordance with the invention. Specifically, the preferred *P. pullulans* microorganism, in addition to its preferential utilization of glucose as compared with fructose, also secretes invertase; therefore, when a sucrose solution is contacted with *P. pullulans*, the invertase serves to degrade the sucrose into glucose and fructose, whereupon the glucose is preferentially utilized in the production of biopolymer. In like manner, the carbohydrate inulin $(C_6H_{10}O_5)_n$, a horny, colorless, amorphous solid derived from dahlia tubers, Jerusalem artichokes and chicory roots, can be employed as a precursor. Here again, excretion of invertase by the *P. pullulans* microorganism serves to produce respective quantities of glucose and fructose, for subsequent selective utilization of glucose. Finally, starch can also serve as a precursor material in accordance with the invention. In such processes, the starch is depolymerized to corn syrup or dextrose, which consists mainly of glucose. An enzymatic isomerization procedure is then undertaken to convert a portion (up to eighty percent) of the glucose to fructose. While the preferred *P. pullulans* does excrete invertase and thus provides a dual functionality as noted, the ability to excrete enzyme is not essential for a given microorganism to function in the context of the invention. For example, a given enzyme-excreting microorganism could be employed for breaking down the precursor material, whereupon another microorganism having the requisite characteristic of preferentially utilizing glucose could then be employed.

The incubation procedure is preferably carried out until the ratio of the concentration of fructose to the concentration of glucose in the material is increased by a factor of at least about 10 times, as compared with the value of the concentration ratio at the outset of incubation. In the case of *P. pullulans*, incubation is advantageously carried out for a period of from about 20 to 50 hours, and more preferably from about 24 to 36 hours. In terms of temperature, the incubation step should be conducted at a temperature from about 20 to 45 degrees C., and more preferably from about 25 to 30 degrees C. Typically, the inoculated material is agitated during the incubation step, and upon termination of incubation the concentrated fructose is subjected to subsequent concentration steps. The latter may involve filtration to remove single cell protein material, passage through an ion exchange resin to remove fructose and separate the latter from pullulan biopolymer, evaporation to produce a concentrated fructose solution, and crystallization to give pure fructose. Obviously, however, the precise recovery and concentration steps performed are dependent upon the desired final product.

DESCRIPTION OF THE PREFERRED EMBODIMENTS

Figure 1:
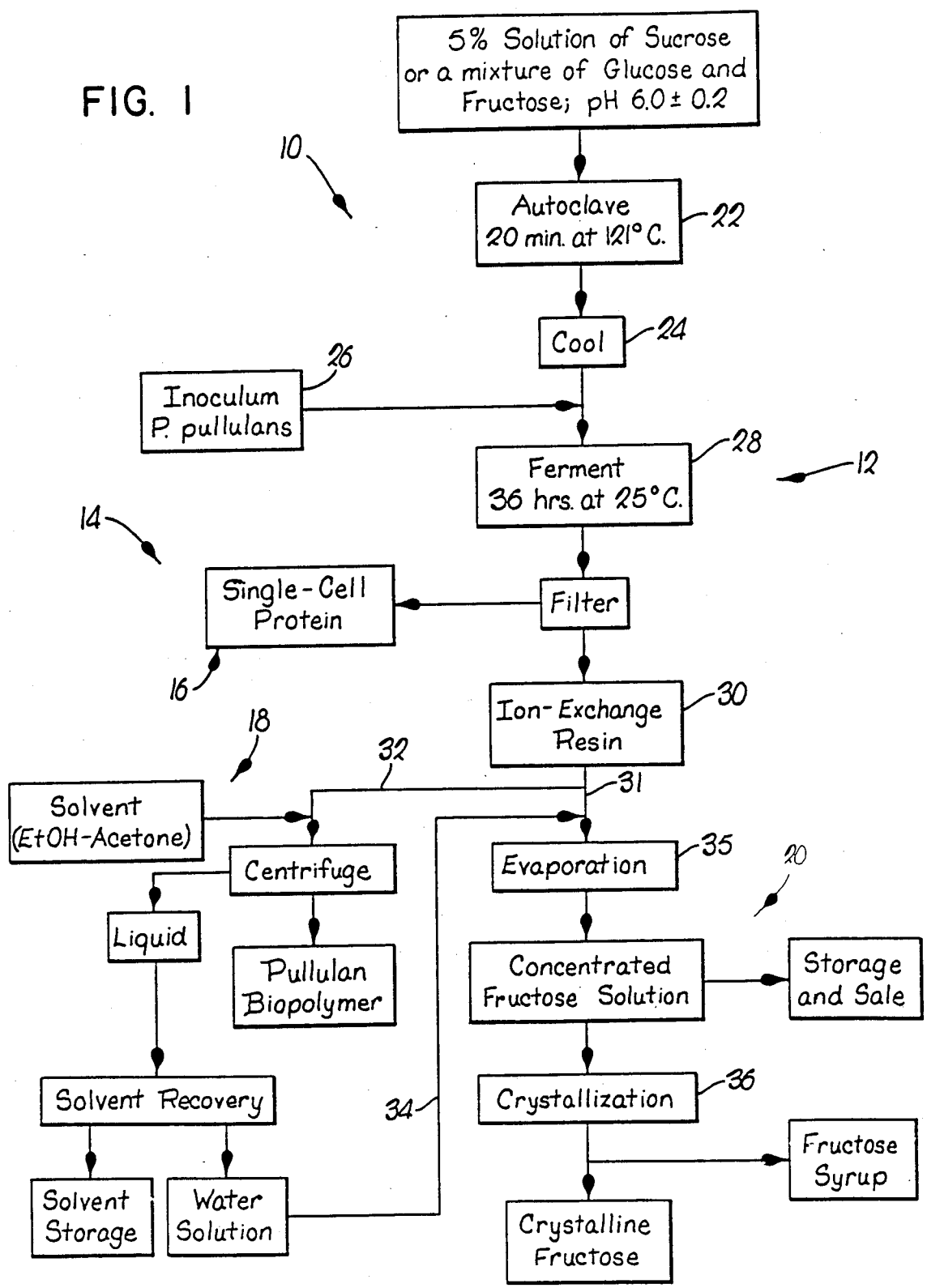
FIG. 1 is a schematic flow diagram illustrating the preferred steps in a process of producing concentrated fructose from a starting material of sucrose or a mixture of glucose and fructose.

Turning now to the drawings, and particularly FIG. 1, a schematic flow diagram is depicted which illustrates the preferred steps in the production of concentrated fructose, using as a starting material a 5% by weight aqueous solution of sucrose, or an aqueous mixture of glucose and fructose (e.g., 2.5% by weight of each). Broadly speaking, the overall process includes material preparation steps indicated at 10, inoculation and incubation of the material as at 12, and recovery procedures 14, the latter including recovery of single cell protein as at 16, recovery of pullulan biopolymer as at 18, and recovery of fructose as at 20.

In more detail, the starting material is prepared simply by mixing the appropriate sugar material in water, either using straight sucrose or a mixture of glucose and fructose. The pH of this mixture should be around 6.0, as indicated. The next step, indicated with reference numeral 22 in FIG. 1, involves autoclaving the aqueous sugar mixture for 20 minutes at 121° C., in order to sterilize the material. The mixture is thereupon cooled, as indicated by reference numeral 24, to a temperature of 25° C., whereupon the cooled material is inoculated (reference numeral 26) with P. pullulans at a level of inoculation of from about 50 to 100 cc. of inoculant per liter of starting solution (the inoculum containing from about $10^7$ to $10^9$ organisms per ml.). The inoculated material is then allowed to ferment or incubate 36 hours at 25° C., using mild aerobic agitation. This serves to keep the inoculum in suspension, and also adds oxygen to the system in order to maintain cell growth. This incubation step is indicated as at 28 in FIG. 1.

At the end of the 36 hours incubation period, the resulting mixture is filtered using a conventional vacuum drum filter and well known techniques, in order to remove, dry, bag and store single cell protein material resulting from the incubation. The filtrate is then passed through an ion exchange resin column containing Dowex 50 resin (see numeral 30, FIG. 1). This serves to adsorb fructose and any remaining glucose onto the resin, whereas the remaining liquid containing pullulan biopolymer is passed from the system through lines 31, 32. Biopolymer is recovered in stage 18 by essentially conventional steps as disclosed in "Bio-plastics and SCP From Starch and Agricultural Wastes", *Process Biochemistry*, Vol 13, No. 3 (1978). Specifically, the pullulan material is first contacted with an equal or greater volume (up to about 2 volumes) of cold (10 degrees C. or colder) solvent such as either acetone or ethanol, whereupon the mixture is centrifuged to remove pullulan biopolymer. The liquid supernatant is then directed to a solvent recovery system wherein the solvent is recovered, and the remaining water solution (which may contain residual sugars), is recycled via line 34 to line 31.

The adsorbed fructose and residual glucose on the ion exchange resin is desorbed by passage of water (25–50 degrees C.) through the ion exchange resin column 30. The resultant solution is then evaporated as at 35, typically at 40–50 degrees C. and vacuum conditions of 700 mm. Hg. This yields concentrated fructose (80–90% by volume) which can be stored in that condition for sale. If desired, further concentration can be effected by cooling to 0–4 degrees C., followed by fractional crystallization (reference numeral 36) to obtain fructose syrup and essentially 100% pure crystalline fructose.

Figure 2:
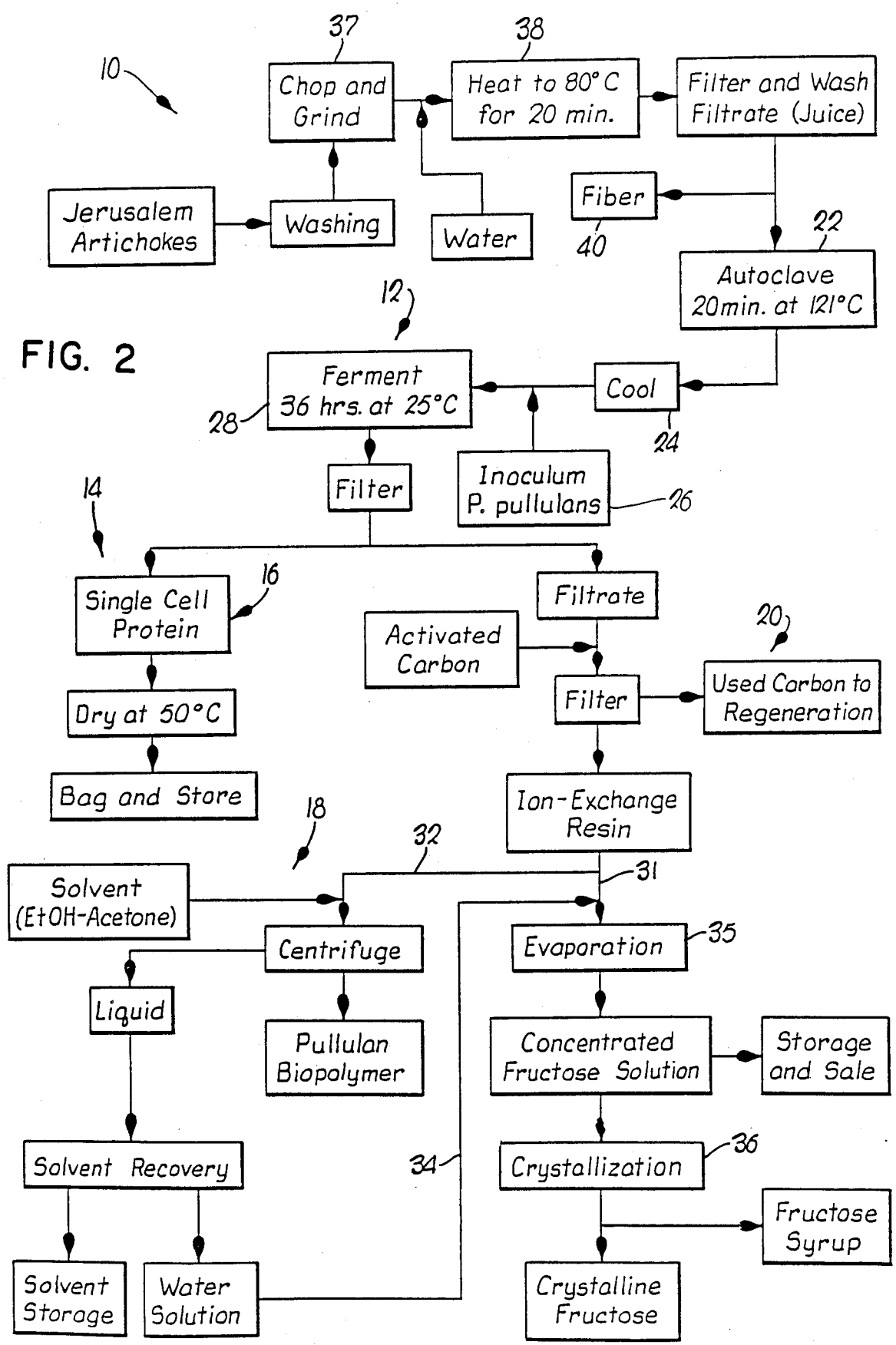
FIG. 2 is a schematic flow diagram similar to that of FIG. 1, but illustrates the preferred method steps to be followed in the production of concentrated fructose using Jerusalem artichokes as a starting material.

The flow diagram of FIG. 2 is in many respects similar to that of FIG. 1, and where identical steps and conditions are followed in FIG. 2, the reference numerals of FIG. 1 are employed.

As in the case of FIG. 1, the FIG. 2 process includes material preparation steps 10, inoculation and incubation as at 12 and recovery procedures 14–20.

The starting material for the FIG. 2 process comprises Jerusalem artichokes, a known source of inulin. In preparative procedures, the artichokes are chopped and ground as at 37, water is added thereto, and the resultant dispersion is heated to 80 degrees C. for 20 minutes (see reference numeral 38) to facilitate inulin recovery. The material is then filtered and washed, with fiber removal as at 40, to recover inulin-containing juice. This latter material is then autoclaved, cooled and inoculated with P. pullulans, all in the manner of the FIG. 1 process and as indicated at reference numerals 22–26. The inoculated liquid is then fermented or incubated as at 28, in order to break down the inulin into respective quantities of glucose and fructose, followed by selective utilization of glucose. Recovery of single cell protein and biopolymer in stages 16, 18 is then carried out in the manner of FIG. 1. Further, recovery of fructose in stage 20 is likewise accomplished as described in connection with FIG. 1.

The foregoing process schema represent exemplary techniques in accordance with the present invention. In addition, specific examples are provided below which demonstrate particular methods employable. In both instances, however, it will be appreacited that those skilled in the art could vary the preferred schema or operational details of the invention without departing from the spirit or scope thereof.

EXAMPLE 1

Preparation of Inoculum

Fungal colonies of *Aureobasidium (Pullularia) pullulans* (ATCC No. 9348) were transferred aseptically from aagar slants to a liquid inoculation medium of the composition shown in Table I.

TABLE I

| Medium Composition | |
|---|---|
| Ingredient | g/liter |
| Sucrose | 50 |
| Yeast extract | 4 |
| $K_2HPO_4$ | 3 |
| NaCl | 1 |
| $(NH_4)_2SO_4$ | 0.6 |
| $MgSO_4.7H_2O$ | 0.2 |
| $FeSO_4.7H_2O$ | 0.1 |
| Tap water, sterile | 1 liter |

These colonies were cultured for 24 hours at 25 degrees C. in an environmentally controlled incubator shaker at an agitation speed of 250 rpm.

EXAMPLE 2

Preparation of Concentrated Fructose from a Solution Containing Equal Parts of Fructose and Glucose A sterile solution of 2.5% by weight fructose and 2.5% by weight glucose in tap water was initially prepared. The following materials (needed for good growth of the *P. pullulans* microorganisms) were then added to 1 liter of the sterile sugar solution: $K_2HPO_4$ 3.0 g; NaCl, 1.0 g; $MgSO_4.7H_2O$, 0.2 g; Yeast Extract, 0.5 g; $(NH_4)_2SO_4$, 0.6 g; $FeSO_4.7H_2O$, 0.1 g. Seven cc of inoculum containing $10^7$ to $10^9$ organisms per ml were then added to 70 ml of the nutrient added sugar solution in a 250 ml Erlenmeyer flask. This was fermented at 25 degrees C. for 96 hours in an incubator-shaker agitated at 250 rpm. Samples were removed at 12 hour intervals and analyzed by conventional high pressure liquid chromatography (HPLC) techniques using a differential refractometer as detector.

As shown in Table II, the glucose essentially disappeared after 36 hours of incubation, and the fructose/glucose concentration ratio was raised by a factor of about 30 times, as compared with the starting ratio, during this time period.

TABLE II

Results of Fermentation of Glucose-Fructose Solution by P. pullulans

| Time, hrs. | Glucose, % by wt. | Fructose, % by weight | Fructose/Glucose |
|---|---|---|---|
| 0 | 2.500 | 2.500 | 1.00:1 |
| 12 | 0.875 | 1.993 | 2.27:1 |
| 24 | 0.188 | 1.487 | 7.81:1 |
| 36 | 0.040 | 1.210 | 30.3:1 |

EXAMPLE 3

Fructose Production from Starting Sucrose Solution

A sterile solution of 5% by weight sucrose in the same medium described in Example 2 was prepared. Fermentation and monitoring were also conducted in the same manner as Example 2. The results are shown in Table 3, where it will be seen that the fructose/glucose concentration ratio was elevated by a factor of about 127 times (79/0.62), as compared with the initial concentration ratio.

TABLE III

Results of Fermentation of 5% Sucrose Solution by P. pullulans

| Time, hrs. | [1]Glucose, % by wt. | [1]Fructose, % by wt. | Sucrose, % by wt. | Fructose/Glucose |
|---|---|---|---|---|
| 0 | 0.590 | 0.370 | 4.0 | |
| 12 | 1.300 | 0.410 | 1.27 | 0.62:1 |
| 24 | 0.940 | 0.550 | 0.96 | 0.51:1 |
| 36 | 0.250 | 1.170 | 0.15 | 4.68:1 |
| 48 | 0.010 | 0.790 | 0.03 | 79:1 |

[1]The sucrose solution contained some glucose and fructose prior to inoculation and incubation.

This example demonstrated that *P. pullulans* excreted invertase which converted the sucrose into glucose and fructose. The glucose was then selectively metabolized by the microorganism.

EXAMPLE 4

Fructose Production from Jerusalem Artichoke Tubers 140 ml. of water was added to 50 g. of washed artichoke tubers, and the tubers were ground to a pulp in a Waring blender. The resultant mash was made up to 200 ml. with tap water and the mixture was then heated to 80° C. for 20 minutes and filtered to remove fiber. The filtrate was sterilized by autoclaving at 121 degrees C. for 20 minutes. After cooling, 20 ml. of the inoculum of Example 1 were added, containing $10^7$ to $10^9$ *P. pullulans* organisms per ml. This broth was placed in a 500 ml. Erlenmeyer flask and fermented at 25 degrees C. for 48 hours in the same manner as Example 2. After fermentation, the broth was filtered, and the solid collected on the filter was dried at 50 degrees C. producing 1.3 g. of single cell protein. The filtrate measured 170 ml. and contained 2.3% by weight or 3.90 g. of fructose. This was mixed with 0.17 g. of activate carbon, agitated for 4 minutes and filtered. The filtrate was passed through an ion-exchange column (Dowex 50) to adsorb fructose. The elutant from the column (using water at 30 degrees C. as the desorbing agent) was then evaporated to about 4.5 ml. to yield a concentrated 90% by weight fructose solution. Upon cooling, fructose crystals were formed which were removed by centrifugation, producing a yield of 2 g. of essentially pure fructose.

The progress of the fermentation was monitored at 12-hour intervals as in previous examples, and the concentrations of glucose and fructose are shown in Table IV. The final fructose/glucose concentration ratio was raised by 130 times, as compared with the starting ratio.

TABLE IV

Fructose Production From Jerusalen Artichokes by P. pullulans

| Time Hrs. | Glucose, % by wt. | Fructose, % by wt. | Fructose/Glucose |
|---|---|---|---|
| 0 | 0.550[1] | 0.510[1] | 1.04:1 |
| 12 | 0.110 | 1.780 | 16.2:1 |
| 24 | 0.090 | 2.010 | 22.3:1 |
| 36 | 0.040 | 1.020 | 25.5:1 |
| 48 | 0.001 | 0.130 | 130:1 |

[1]The presence of these small amounts of glucose and fructose in the fermentation broth at time zero results from the fact that Jerusalem artichoke tubers contain these sugars in small quantities independent of inulin.

The carbohydrate in artichokes, dahlias and chicory is inulin, a polysaccharide containing one glucose unit to 20-35 fructose units. *P. pullulans* excretes both inulase and invertase, which break down the polymer into the basic units, glucose and fructose, whereupon the microorganism preferentially utilizes glucose.

It will also be understood that the present invention differs fundamentally from prior techniques of isomerization of glucose to fructose. For example, Strandberg et al. "Free and Immobilized Glucose Isomerase from *Streptomyces phaeochromogenes*", *Applied Microbiology,* April 1971, pp. 588-593, described use of a microorganism which secretes an enzyme, referred to as glucose isomerase, which catalyzes the isomerization of glucose to fructose. However, in such isomerization techniques there is no actual metabolic utilization of glucose by a microorganism and the total content of sugar in the system remains stable. In the instant invention, however, glucose is used during the incubation step, and the total sugar content of the system decreases. Of course in the case of the preferred *P. pullulans,* glucose is metabolized and used in the production of biopolymer.

In addition, while the incubation step hereof can advantageously be terminated upon a rise in the fructose/glucose concentration ratio as previously discussed, other termination points can be selected. For example, in some instances the absolute concentration of fructose rises to a maximum and then falls, indicating that some fructose is being utilized after the fructose maximum is reached. In some cases it may be desired to terminate the incubation at or about this fructose concentration maximum, even though the fructose/glucose concentration ratio is somewhat lower than what could be achieved through continued incubation.

I claim:

1. A process for producing concentrated fructose, comprising the steps of:
   contacting a material including quantities of fructose and glucose with *Pullularia pululans* for preferentially and metabolically utilizing glucose as compared with fructose;
   incubating the Pullularia pululans to preferentially and metabolically utilize said glucose as compared with said fructose, and to decrease the total sugar content of said material;
   terminating said incubation when the concentration of fructose in said material is at a desired level which is higher than the concentration of said glucose in said material; and
   recovering fructose.

2. The process of claim 1, including the step of obtaining said material by the degradation of a precursor material to yield respective quantities of glucose and fructose.

3. The process of claim 2, said precursor material comprising sucrose.

4. The process of claim 2, said precursor material comprising inulin.

5. The process of claim 1, including the step of incubating said material for a period of from about 20 to 50 hours.

6. The process of claim 1, including the step of incubating said material at a temperature of from about 20 to 45 degrees C.

7. The process of claim 1, said material comprising an aqueous mixture of fructose and glucose.

8. The process of claim 1, including the step of agitating said material during said incubation step.

9. The process of claim 1, including the step of terminating said incubation step when the ratio of the concentration of fructose to the concentration of glucose in said material is raised by a factor of at least about 10 times, as compared with the value of said ratio at the outset of said incubation step.

10. The process of claim 1, said recovery step comprising the step of terminating said incubation and subjecting the incubated material to subsequent concentration.

11. The process of claim 10, said subsequent concentration step comprising evaporation of said incubated material.

12. The process of claim 11, including the step of crystallizing fructose from said evaporated material.

13. The process of claim 1, including the step of filtering said material after said incubation thereof.

14. The process of claim 13, including the step of contacting said filtered material with an ion exchange resin.

15. A process for producing concentrated fructose, comprising the steps of:
   contacting a material including quantities of fructose and glucose with Pullularia pululans;
   incubating said contacted material at a temperature of from about 20 to 45 degrees C. and under conditions for causing said Pullularia pululans to preferentially and metabolically utilize glucose as compared to fructose, and to decrease the total sugar content of said material;
   terminating said incubation after a period of time when the ratio of the concentration of fructose to the concentration of glucose in said material is raised by a factor of at least about 10 times, as compared with the value of said ratio at the outset of said incubation step, said time period being from about 20 to 50 hours; and
   recovering fructose.

* * * * *